United States Patent
Sainani et al.

(10) Patent No.: US 10,882,929 B2
(45) Date of Patent: Jan. 5, 2021

(54) PROCATALYST FOR POLYMERIZATION OF OLEFINS

(71) Applicant: SABIC GLOBAL TECHNOLOGIES B.V., Bergen Op Zoom (NL)

(72) Inventors: Jaiprakash Brijlal Sainani, Geleen (NL); Akhlaq Moman, Geleen (NL)

(73) Assignee: SABIC GLOBAL TECHNOLOGIES B.V., Bergen Op Zoom (NL)

(*) Notice: Subject to any disclaimer, the term of this patent is extended or adjusted under 35 U.S.C. 154(b) by 132 days.

(21) Appl. No.: 16/337,177

(22) PCT Filed: Sep. 29, 2017

(86) PCT No.: PCT/EP2017/074758
§ 371 (c)(1),
(2) Date: Mar. 27, 2019

(87) PCT Pub. No.: WO2018/060413
PCT Pub. Date: Apr. 5, 2018

(65) Prior Publication Data
US 2019/0225718 A1    Jul. 25, 2019

(30) Foreign Application Priority Data
Sep. 29, 2016  (EP) .................................. 16191490

(51) Int. Cl.
*C08F 10/06* (2006.01)
*C08F 110/06* (2006.01)
*C07C 233/69* (2006.01)

(52) U.S. Cl.
CPC .......... *C08F 10/06* (2013.01); *C07C 233/69* (2013.01); *C08F 110/06* (2013.01)

(58) Field of Classification Search
CPC ....... C08F 10/06; C08F 110/06; C07C 233/69
See application file for complete search history.

(56) References Cited

U.S. PATENT DOCUMENTS

| 4,946,816 A | 8/1990 | Cohen et al. |
| 6,780,808 B2 | 8/2004 | Wagner et al. |
| 2011/0269928 A1 | 11/2011 | Fujiwara et al. |
| 2013/0225398 A1 | 8/2013 | Chen et al. |
| 2015/0299346 A1 | 10/2015 | Chen et al. |
| 2019/0225715 A1 | 7/2019 | Moman et al. |
| 2019/0225716 A1 | 7/2019 | Sainani et al. |
| 2020/0048378 A1 | 2/2020 | Moman et al. |
| 2020/0055968 A1 | 2/2020 | Moman et al. |

FOREIGN PATENT DOCUMENTS

| EP | 0613912 A2 | 9/1994 | |
| WO | 2011106494 A1 | 9/2011 | |
| WO | 2013124063 A1 | 8/2013 | |
| WO | 2014001257 A1 | 1/2014 | |
| WO | 2015091983 A1 | 6/2015 | |
| WO | 2015091984 A1 | 6/2015 | |
| WO | 2015185489 A1 | 12/2015 | |
| WO | 2015185490 A1 | 12/2015 | |
| WO | 2015193291 A1 | 12/2015 | |
| WO | WO-2015185489 A1 * | 12/2015 | ............ C08F 110/06 |

OTHER PUBLICATIONS

International Search Report for International Application No. PCT/EP2017/074758, International Filing Date Sep. 29, 2017, dated Dec. 13, 2017, 4 pages.
Written Opinion for International Application No. PCT/EP2017/074758, International Filing Date Sep. 29, 2017, dated Dec. 13, 2017, 5 pages.

* cited by examiner

*Primary Examiner* — Catherine S Branch
(74) *Attorney, Agent, or Firm* — Cantor Colburn LLP

(57) ABSTRACT

The present invention relates to a procatalyst comprising the compound represented by formula A as an internal electron donor (Formula A), wherein R is hydrogen or a methyl group, N is nitrogen atom; O is oxygen atom; and C is carbon atom. The present invention also relates to a process for preparing said polymerization procatalyst and to a polymerization catalyst system comprising said procatalyst, a co-catalyst and optionally an external electron donor. Furthermore, the present invention relates to a polyolefin obtainable by the process according to the present invention and to the use of the compound of formula A as in internal electron donor in catalysts for polymerization of olefins.

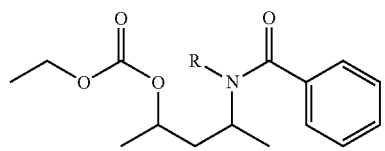

Formula A

17 Claims, No Drawings

PROCATALYST FOR POLYMERIZATION OF OLEFINS

CROSS REFERENCE TO RELATED APPLICATIONS

This application is a National Stage application of PCT/EP2017/074758, filed Sep. 29, 2017, which claims the benefit of European Application No. 16191490.8, filed Sep. 29, 2016, both of which are incorporated by reference in their entirety herein.

The invention relates to a procatalyst for polymerization of olefins comprising an internal electron donor according to Formula A. The invention also relates to a method for preparing said procatalyst including said internal electron donor and to the procatalyst directly obtained via said process. Furthermore, the invention is directed to a catalyst system for polymerization of olefins comprising said procatalyst, a co-catalyst and optionally an external electron donor. Moreover, the use of a compound of Formula A as internal donor is part of the invention. In addition, the invention is related to a process of making polyolefins by contacting at least one olefin with said catalyst system and to polyolefins obtainable by said process. Moreover, the present invention relates to polymers obtained by polymerization using said procatalyst and to the shaped articles of said polymers and to the shaped articles of said polymers. In addition, the present invention is related to a compound of Formula A.

Catalyst systems and their components that are suitable for preparing a polyolefin are generally known. One type of such catalysts is generally referred to as Ziegler-Natta catalysts. The term "Ziegler-Natta" is known in the art and it typically refers to catalyst systems comprising a transition metal-containing solid catalyst compound (also typically referred to as a procatalyst); an organometallic compound (also typically referred to as a co-catalyst) and optionally one or more electron donor compounds (e.g. external electron donors). The transition metal-containing solid catalyst compound comprises a transition metal halide (e.g. titanium halide, chromium halide, hafnium halide, zirconium halide, vanadium halide) supported on a metal or metalloid compound (e.g. a magnesium compound or a silica compound). An overview of such catalyst types is for example given by T. Pullukat and R. Hoff in Catal. Rev.—Sci. Eng. 41, vol. 3 and 4, 389-438, 1999. The preparation of such a procatalyst is for example disclosed in WO96/32427 A1.

There is an on-going need in industry for phthalate free catalyst for preparing polymers, in particular polyolefins. From WO2014001257 of the present applicant is known the use of the following, phthalate free compound (I) as an internal electron donor for a procatalyst:

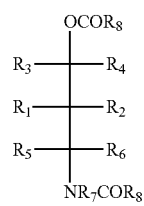

Formula (I)

wherein both $R_8$ groups are an aromatic group, to provide a so-called amidobenzoate internal electron donor.

It is an object of the present invention to provide a novel phthalate free procatalyst for the polymerization of olefins; said novel procatalyst comprising a novel internal electron donor. It is a further object of the present invention is to provide a procatalyst which shows good catalyst performance as well as provide a polyolefin having good polymer properties.

At least one of the aforementioned objects of the present invention is achieved with a first aspect of the present invention, being a procatalyst for the polymerization of olefins, which procatalyst comprises the compound represented by Formula A as an internal electron donor:

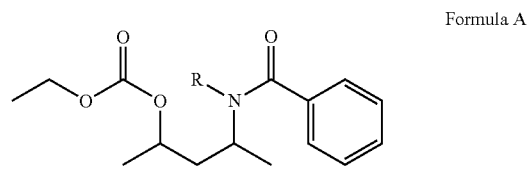

Formula A wherein in Formula A: the R group is either a hydrogen atom (H) or a methyl group (—$CH_3$) to form respectively A-H or A-Me. Moreover, in Formula A: N is nitrogen atom; O is oxygen atom; and the corners of the solid lines are depicting a carbon atom (C). The compound according to Formula A is a so-called carbonate-carbamate compound, having a carbonate moiety (—O—C(=O)—O) linked to a carbamate moiety (—N(R)—C(=O)—).

Definitions

The following definitions are used in the present description and claims to define the stated subject matter. Other terms not cited below are meant to have the generally accepted meaning in the field.

"Ziegler-Natta catalyst" as used in the present description means: a transition metal-containing solid catalyst compound comprises Ziegler-Natta catalytic species supported on a metal or metalloid compound (e.g. a magnesium compound or a silica compound).

"Ziegler-Natta catalytic species" or "catalytic species" as used in the present description means: a transition metal-containing species comprises a transition metal halide selected from titanium halide, chromium halide, hafnium halide, zirconium halide and vanadium halide.

"internal donor" or "internal electron donor" or "ID" as used in the present description means: an electron-donating compound containing one or more atoms of oxygen (O) and/or nitrogen (N).

"external donor" or "external electron donor" or "ED" as used in the present description means: an electron-donating compound used as a reactant in the polymerisation of olefins. It comprises at least one functional group that is capable of donating at least one pair of electrons to a metal atom.

"activator" as used in the present description means: an electron-donating compound containing one or more atoms of oxygen (O) and/or nitrogen (N) which is used during the synthesis of the procatalyst prior to or simultaneous with the addition of an internal donor.

"activating compound" as used in the present description means: a compound used to activate the solid support prior to contacting it with the catalytic species.

"modifier" or "Group 13- or transition metal modifier" as used in the present description means: a metal modifier comprising a metal selected from the metals of Group 13 of the IUPAC Periodic Table of elements and transition metals. Where in the description the terms metal modifier or metal-based modifier is used, Group 13- or transition metal modifier is meant.

"procatalyst" and "catalyst component" as used in the present description have the same meaning: a component of a catalyst composition generally comprising a solid support, a transition metal-containing catalytic species and optionally one or more internal donor.

"halide" or "halogen" as used in the present description means: an ion selected from the group of: fluoride (F—), chloride (Cl—), bromide (Br—) or iodide (I—).

"Heteroatom" as used in the present description means: an atom other than carbon or hydrogen. However, as used herein—unless specified otherwise, such as below,—when "one or more heteroatoms" is used one or more of the following is meant: F, Cl, Br, I, N, O, P, B, S or Si. Thus a heteroatom also includes halides.

"hydrocarbyl" as used in the present description means: is a substituent containing hydrogen and carbon atoms, or linear, branched or cyclic saturated or unsaturated aliphatic radical, such as alkyl, alkenyl, alkadienyl and alkynyl; alicyclic radical, such as cycloalkyl, cycloalkadienyl cycloalkenyl; aromatic radical, such as monocyclic or polycyclic aromatic radical, as well as combinations thereof, such as alkaryl and aralkyl.

"substituted hydrocarbyl" as used in the present description means: is a hydrocarbyl group that is substituted with one or more non-hydrocarbyl substituent groups.

A non-limiting example of a non-hydrocarbyl substituent is a heteroatom. Examples are alkoxycarbonyl (viz. carboxylate) groups. When in the present description "hydrocarbyl" is used it can also be "substituted hydrocarbyl", unless stated otherwise.

"alkyl" as used in the present description means: an alkyl group being a functional group or side-chain consisting of carbon and hydrogen atoms having only single bonds. An alkyl group may be straight or branched and may be un-substituted or substituted. An alkyl group also encloses aralkyl groups wherein one or more hydrogen atoms of the alkyl group have been replaced by aryl groups.

"aryl" as used in the present description means: an aryl group being a functional group or side-chain derived from an aromatic ring. An aryl group and may be un-substituted or substituted with straight or branched hydrocarbyl groups. An aryl group also encloses alkaryl groups wherein one or more hydrogen atoms on the aromatic ring have been replaced by alkyl groups.

"alkoxide" or "alkoxy" as used in the present description means: a functional group or side-chain obtained from an alkyl alcohol. It consists of an alkyl bonded to a negatively charged oxygen atom.

"aryloxide" or "aryloxy" or "phenoxide" as used in the present description means: a functional group or side-chain obtained from an aryl alcohol. It consists of an aryl bonded to a negatively charged oxygen atom.

"Grignard reagent" or "Grignard compound" as used in the present description means: a compound or a mixture of compounds of formula $R^4_zMgX^4_{2-z}$ ($R^4$, z, and $X^4$ are as defined below) or it may be a complex having more Mg clusters, e.g. $R^4Mg_3Cl_2$.

"polymer" as used in the present description means: a chemical compound comprising repeating structural units, wherein the structural units are monomers.

"olefin" as used in the present description means: an alkene.

"olefin-based polymer" or "polyolefin" as used in the present description means: a polymer of one or more alkenes.

"propylene-based polymer" as used in the present description means: a polymer of propylene and optionally a comonomer.

"polypropylene" as used in the present description means: a polymer of propylene.

"copolymer" as used in the present description means: a polymer prepared from two or more different monomers.

"monomer" as used in the present description means: a chemical compound that can undergo polymerization.

"MWD" or "Molecular weight distribution" as used in the present description means: the same as "PDI" or "polydispersity index". It is the ratio of the weight-average molecular weight ($M_w$) to the number average molecular weight ($M_n$), viz. $M_w/M_n$, and is used as a measure of the broadness of molecular weight distribution of a polymer. $M_w$ and $M_n$ are determined by GPC using a Waters 150° C. gel permeation chromatograph combined with a Viscotek 100 differential viscosimeter; the chromatograms were run at 140° C. using 1,2,4-trichlorobenzene as a solvent; the refractive index detector was used to collect the signal for molecular weights.

"APP wt. %" or "weight percentage of atactic polypropylene" as used in the present description means: the fraction of polypropylene obtained in a slurry polymerization that is retained in the solvent. APP can be determined by taking 100 ml of the filtrate ("y" in millilitres) obtained during separation from polypropylene powder after slurry polymerization ("x" in grammes). The solvent is dried over a steam bath and then under vacuum at 60° C.

That yields APP ("z" in grammes). The total amount of APP ("q" in grammes) is (y/100)*z. The weight percentage of APP is (q/q+x))*100%.

"XS" or "xylene soluble fraction" as used in the present description means: the weight percentage (wt. %) of soluble xylene in the isolated polymer, measured according to ASTM D 5492-10.

"polymerization conditions" as used in the present description means:

temperature and pressure parameters within a polymerization reactor suitable for promoting polymerization between the catalyst composition and an olefin to form the desired polymer. These conditions depend on the type of polymerization used.

"production rate" or "yield" as used in the present description means: the amount of kilograms of polymer produced per gram of procatalyst consumed in the polymerization reactor per hour, unless stated otherwise.

"MFR" or "Melt Flow rate" as used in the present description is measured at a temperature of 230° C. with 2.16 kg load and measured according to ISO 1133:2005.

Unless stated otherwise, when it is stated that any R group is "independently selected from" this means that when several of the same R groups are present in a molecule they may have the same meaning or they may not have the same meaning. For example, for the compound $R_2M$, wherein R is independently selected from ethyl or methyl, both R groups may be ethyl, both R groups may be methyl or one R group may be ethyl and the other R group may be methyl.

The present invention is described below in more detail. All embodiments described with respect to one aspect of the present invention are also applicable to the other aspects of the invention, unless otherwise stated.

DESCRIPTION OF THE INVENTION

It has been surprisingly found that the procatalyst comprising the compound of Formula A as an internal electron donor shows good control of stereochemistry.

In an embodiment of the first aspect of the invention—discussed above—R is hydrogen; in other words said carbamate moiety is —NH—C(=O)—. In a further embodiment of said first aspect, R is a methyl group; in other words said carbamate moiety is —N(CH$_3$)—C(=O)—. Both of these embodiments are both shown below:

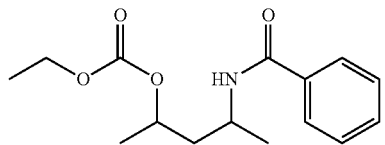 [SMILES: CCOC(=O)OC(C)CC(C)NC(=O)c1ccccc1]

ethyl (4-benzamidopentan-2-yl) carbonate (Formula A-H)

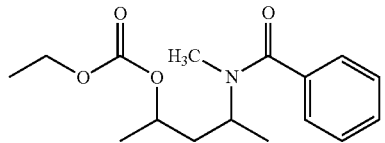 [SMILES: CCOC(=O)OC(C)CC(C)N(C)C(=O)c1ccccc1]

ethyl (4-(N-methylbenzamido)pentan-2-yl) carbonate (Formula A-Me)

In an embodiment of said first aspect, said procatalyst comprises titanium supported on a solid magnesium-containing support. In other words, the catalytic species is a titanium species that is supported by a solid support, comprising magnesium.

In an embodiment, the procatalyst comprises in wt. % based on the total weight of the procatalyst: magnesium: from 13 to 24, preferably from 14 to 22; titanium: from 1 to 5, preferably from 1.5 to 4.

In a second aspect, the present invention relates to a process for preparing the procatalyst according to the present invention, comprising contacting a magnesium-containing support with a halogen-containing titanium compound and an internal electron donor, wherein the internal electron donor is represented by Formula A (as above), wherein the R group is either a hydrogen atom (H) or a methyl group (—CH$_3$). N is nitrogen atom; O is oxygen atom; and C is carbon atom.

In an embodiment of said second aspect, said method comprises the steps of:

i) contacting a compound $R^4_z MgX^4_{2-z}$ with an alkoxy- or aryloxy-containing silane compound to give a first intermediate reaction product, being a solid $Mg(OR^1)_x X^1_{2-x}$, wherein: $R^4$ and $R^1$ are each a linear, branched or cyclic hydrocarbyl group independently selected from alkyl, alkenyl, aryl, aralkyl, alkoxycarbonyl or alkylaryl groups, and one or more combinations thereof; wherein said hydrocarbyl group may be substituted or unsubstituted, may contain one or more heteroatoms and preferably has from 1 to 20 carbon atoms; preferably $R^4$ is phenyl or butyl; $X^4$ and $X^1$ are each independently selected from the group consisting of fluoride (F—), chloride (Cl—), bromide (Br—) or iodide (I—), preferably chloride; z is in a range of larger than 0 and smaller than 2, e.g. z=1, being 0<z<2; x is in a range of larger than 0 and smaller than 2, being 0<x<2, e.g. x=1;

ii) optionally contacting the first intermediate reaction product obtained in step ii) with at least one activating compound selected from the group formed by activating electron donors and metal alkoxide compounds of formula $M^1(OR^2)_{v-w}(OR^3)_w$ or $M^2(OR^2)_{v-w}(R^3)_w$, to obtain a second intermediate product; wherein: $M^1$ is a metal selected from the group consisting of Ti, Zr, Hf, Al or Si; $M^2$ is a metal being Si; v is the valency of M1 or $M^2$ respectively; w is smaller than v; $R^2$ and $R^3$ are each a linear, branched or cyclic hydrocarbyl group independently selected from alkyl, alkenyl, aryl, aralkyl, alkoxycarbonyl or alkylaryl groups, and one or more combinations thereof; wherein said hydrocarbyl group may be substituted or unsubstituted, may contain one or more heteroatoms, and preferably has from 1 to 20 carbon atoms; for example v being either 3 or 4; and iii) contacting the first or second intermediate reaction product, obtained respectively in step i) or ii), with a halogen-containing Ti-compound and said internal electron represented by Formula A.

In other words, a process which comprises the steps of: i) contacting a compound $R^4_z MgX^4_{2-z}$ wherein $R^4$ is aromatic, aliphatic or cyclo-aliphatic group containing 1 to 20 carbon atoms, preferably butyl or phenyl, $X^4$ is a halide, and z is in a range of larger than 0 and smaller than 2, preferably 1; with an alkoxy- or aryloxy-containing silane, preferably tetraalkoxy silane (e.g. tetraethoxy silane) to give a first intermediate reaction product; ii) contacting the solid $Mg(OR^1)_x X_{2-x}$ with at least one, preferably two, activating compound selected from the group formed by electron donors and compounds of formula $M^1(OR^2)_{v-w}(OR^3)_w$, wherein M is Ti, Zr, Hf, Al or Si and $M^2(OR^2)_{v-w}(R^3)_w$, wherein $M^2$ is Si, each $R^2$ and $R^3$, independently, represent an alkyl, alkenyl or aryl group, v is the valency of M (either $M^1$ or $M^2$), v being either 3 or 4 and w is smaller than v; and iii) contacting the second intermediate reaction product with a halogen-containing Ti-compound, an internal electron donor represented by formula A, wherein the R group is either a hydrogen atom (H) or a methyl group (—CH$_3$); N is a nitrogen atom; and O is an oxygen atom; preferably wherein the first intermediate reaction product is contacted with an alcohol (e.g. ethanol) and a titanium tetraalkoxide (e.g. titanium tetraethoxide) in step ii).

In an embodiment, the process comprises the steps of:

i) contacting a compound $R^4_z MgX^4_{2-z}$ with an alkoxy- or aryloxy-containing silane compound to give a first intermediate reaction product, being a solid $Mg(OR^1)_x X^1_{2-x}$;

iii) contacting the first intermediate reaction product, obtained in step i) with a halogen-containing Ti-compound and said internal electron donor being a compound represented by Formula A.

In an embodiment, the process comprises the steps of:

i) contacting a compound $R^4_z MgX^4_{2-z}$ with an alkoxy- or aryloxy-containing silane compound to give a first intermediate reaction product, being a solid $Mg(OR^1)_x X^1_{2-x}$;

ii) contacting the first intermediate reaction product obtained in step i) with at least one activating compound selected from the group consisting of activating electron donors and metal alkoxide compounds of formula $M^1(OR^2)_{v-w}(OR^3)_w$ or $M^2(OR^2)_{v-w}(R^3)_w$, to obtain a second intermediate product; and iii) contacting the second intermediate reaction product, obtained in step ii), with a halogen-containing Ti-compound and said internal electron donor being a compound represented by Formula A.

In a specific embodiment, the process comprises the steps of:

i) contacting a compound $R^4_z MgX^4_{2-z}$ with an alkoxy- or aryloxy-containing silane compound $Si(OR^5)_4$ to give a first intermediate reaction product: a solid $Mg(OR^1)_x X^1_{2-x}$;

ii) contacting the first intermediate reaction product obtained in step i) with an activating electron donor and a metal alkoxide compounds of formula $M^1(OR^2)_{v-w}(OR^3)_w$ to obtain a second intermediate product; and iii) contacting the second intermediate reaction product, obtained in step ii), with a halogen-containing Ti-compound and said internal electron donor being a compound represented by Formula A.

In an embodiment, said alkoxy- or aryloxy-containing silane being $Si(OR^5)_{4-n}(R^6)_n$ wherein: $R^5$ and $R^6$ are each independently selected from linear, branched or cyclic hydrocarbyl group independently selected from alkyl, alkenyl, aryl, aralkyl, alkoxycarbonyl or alkylaryl groups (preferably alkyl groups), and one or more combinations thereof; wherein said hydrocarbyl group may be substituted or unsubstituted, may contain one or more heteroatoms and preferably has from 1 to 20 carbon atoms; more preferably C1 to C4 alkyl; and n is in range of 0 to 4, preferably n is from 0 up to and including 1. In an embodiment, the $OR^5$ group of the silane compound will become the $OR^1$ group in the first intermediate reaction product. In an embodiment $R^5$ is another name for $R^1$, being the same group. In an embodiment, the $X^4$ group of the magnesium compound will become the X1 group in the first intermediate reaction product. In an embodiment, $X^4$ is another name for $X^1$, being the same group. In a more preferred embodiment said alkoxy- or aryloxy-containing silane being $Si(OR^5)_4$ wherein $R^5$ is C1 to C4 alkyl, most preferably all $R^5$ are ethyl, being tetraethoxy silane (TES).

In a further embodiment, an activator is used, preferably in step iii). In a further embodiment, said activator is selected from the group consisting of benzamides, alkylbenzoates, and mono-esters. In a further embodiment, said activator is selected from the group consisting of ethyl acetate, amyl acetate, butyl acetate, ethyl acrylate, methyl methacrylate, and isobutyl methacrylate, benzamide, methylbenzamide, dimethylbenzamide, methylbenzoate, ethylbenzoate, n-propylbenzoate, iso-propylbenzoate, n-butylbenzoate, 2-butylbenzoate, and t-butylbenzoate. In a preferred embodiment, ethyl acetate (EA) or ethyl benzoate (EB) is used as activator.

In another embodiment a butyl Grignard (preferably BuMgCl or n-BuMgCl) is used to prepare the procatalyst composition. In another embodiment a phenyl Grignard (preferably PhMgCl) is used to prepare the procatalyst composition.

Several specific embodiments are the following: A-H+EA; A-H+EB; A-Me+EA; A-Me+EB; A-H+Bu-G; A-Me+Bu-G; A-H+Ph-G; A-Me+Ph-G; A-H+nBuMgCl; A-Me+nBuMgCl; A-H+PhMgCl; A-Me+PhMgCl; A-H+EA+nBuMgCl; A-H+EB+nBuMgCl; A-Me+EA+nBuMgCl; A-Me+EB+nBuMgCl; A-H+EA+PhMgCl; A-H+EB+PhMgCl; A-Me+EA+PhMgCl; A-Me+EB+PhMgCl. Wherein: A-H means a procatalyst for the polymerization of olefins, which procatalyst comprises the compound represented by Formula A as an internal electron donor wherein in Formula A, R=H; A-Me means a procatalyst for the polymerization of olefins, which procatalyst comprises the compound represented by Formula A as an internal electron donor wherein in Formula A, R=Me; EA means that ethyl acetate is used as activator during step iii) of the process to prepare the procatalyst; EB means that ethyl benzoate is used as activator during step iii) of the process to prepare the procatalyst; Bu-G means that during step i) of the process to prepare the procatalyst a butyl Grignard is used, being a compound $R^4_z MgX^4_{2-z}$ wherein $R^4$ is butyl; Ph-G means that during step i) of the process to prepare the procatalyst a phenyl Grignard is used, being a compound $R^4_z MgX^4_{2-z}$ wherein $R^4$ is phenyl; n-BuMgCl means that during step i) of the process to prepare the procatalyst as compound $R^4_z MgX^4_{2-z}$ n-BuMgCl is used; and PhMgCl means that during step i) of the process to prepare the procatalyst as compound $R^4_z MgX^4_{2-z}$ PhMgCl is used.

In an embodiment, the procatalyst has been modified by using a group 13- or transition metal modifier. This embodiment is applicable to all specific embodiments discussed above.

In an embodiment, $TiCl_4$ is used in step iii) as the catalytic species. This embodiment is applicable to all specific embodiments discussed above.

In a further embodiment of said second aspect, during step ii) as activating compounds an alcohol is used as activating electron donor and titanium tetraalkoxide is used as metal alkoxide compound. More preferably a combination of ethanol and titanium tetraethoxide (TET). This embodiment is applicable to all specific embodiments discussed above.

In another aspect, the present invention relates to a polymerization catalyst system comprising the procatalyst according to the present invention, a co-catalyst and optionally an external electron donor.

In another aspect, the present invention relates to a process of making a polyolefin, preferably a polypropylene, by contacting at least one olefin with the catalyst system according to the present invention. In an embodiment of this aspect, propylene is used as said olefin to obtain polypropylene.

In another aspect, the present invention relates to polyolefin, preferably a polypropylene obtainable by the process of making a polyolefin according to the present invention.

In another aspect, the present invention relates to shaped article, comprising the polyolefin, preferably the polypropylene according to the above aspect of the present invention.

In another aspect, the present invention relates to the use of the compound represented by Formula A as an internal electron donor in a procatalyst for the polymerization of at least one olefin, wherein the R group is either a hydrogen atom (H) or a methyl group (—$CH_3$). N is nitrogen atom; O is oxygen atom; and C is carbon atom.

In another aspect, the present invention relates to a compound of Formula A wherein the R group is either a hydrogen atom (H) or a methyl group (—$CH_3$). N is nitrogen atom; O is oxygen atom; and C is carbon atom.

Preferably, the procatalyst according to the invention comprises the compound having formula A as the only internal electron donor in a Ziegler-Natta catalyst composition.

The compound according to Formula A can be made by any method known in the art. In this respect, reference is made to J. Chem. Soc. Perkin trans. I 1994, 537-543 and to Org. Synth. 1967, 47, 44. A detailed description of regarding the synthesis of these compounds can be found in WO2015091984 A1 of the same applicant, page 51 line 10 to page 53, line 3, which section is incorporated here by reference.

The molar ratio of the internal donor of Formula A relative to the magnesium can be from 0.01 to 0.75, preferably from 0.02 to 0.5. Preferably, this molar ratio is from 0.03 to 0.3.

The process for preparing the procatalyst according to the present invention comprises contacting a magnesium-containing support with a halogen-containing titanium compound and an internal donor, wherein the internal electron donor is the compound represented by the Formula A. The present invention is related to Ziegler-Natta type procatalyst and catalyst system. A Ziegler-Natta type procatalyst generally comprising a solid support, a transition metal-containing catalytic species and an internal donor. The present invention moreover relates to a catalyst system comprising a Ziegler-Natta type procatalyst, a co-catalyst and optionally an external electron donor.

The transition metal-containing solid catalyst compound comprises a transition metal halide (e.g. titanium halide, chromium halide, hafnium halide, zirconium halide, vanadium halide) supported on a metal or metalloid compound (e.g. a magnesium compound or a silica compound). Specific examples of several types of Ziegler-Natta catalyst are disclosed below. Preferably, the present invention provides a magnesium-based supported titanium halide catalyst comprising an internal donor.

The magnesium-containing support and halogen-containing titanium compounds used in the process according to the present invention are known in the art as typical components of a Ziegler-Natta catalyst composition. Any of said Ziegler-Natta catalytic species known in the art can be used in the process according to the present invention. For instance, synthesis of such titanium-magnesium based catalyst compositions with different magnesium-containing support-precursors, such as magnesium halides, magnesium alkyls and magnesium aryls, and also magnesium alkoxy and magnesium aryloxy compounds for polyolefin production, particularly of polypropylenes production are described for instance in U.S. Pat. No. 4,978,648, WO96/32427A1, WO01/23441 A1, EP1283 222A1, EP1222 214B1; U.S. Pat. Nos. 5,077,357; 5,556,820; 4,414,132; 5,106,806 and 5,077,357 but the present process is not limited to the disclosure in these documents.

EP 1 273 595 of Borealis Technology discloses a process for producing an olefin polymerization procatalyst in the form of particles having a predetermined size range, said process comprising: preparing a solution a complex of a Gp IIa metal and an electron donor by reacting a compound of said metal with said electron donor or a precursor thereof in an organic liquid reaction medium; reacting said complex, in solution, with at least one compound of a transition metal to produce an emulsion the dispersed phase of which contains more than 50 mol % of the Gp IIa metal in said complex; maintaining the particles of said dispersed phase within the average size range 10 to 200 mu m by agitation in the presence of an emulsion stabilizer and solidifying said particles; and recovering, washing and drying said particles to obtain said procatalyst.

EP 0 019 330 of Dow discloses a Ziegler-Natta type catalyst composition. Said olefin polymerization catalyst composition comprising: a) a reaction product of an organo aluminum compound and an electron donor, and b) a solid component which has been obtained by halogenating a magnesium compound with the formula $MgR^1R^2$ wherein $R^1$ is an alkyl, aryl, alkoxide or aryloxide group and $R^2$ is an alkyl, aryl, alkoxide or aryloxide group or halogen, with a halide of tetravalent titanium in the presence of a halohydrocarbon, and contacting the halogenated product with a tetravalent titanium compound.

The procatalyst may be produced by any method known in the art using the present internal electron donor according for Formula A. The procatalyst may for example be produced as disclosed in WO96/32426A; this document discloses a process for the polymerization of propylene using a catalyst comprising a procatalyst obtained by a process wherein a compound with formula $Mg(OAlk)_xCl_y$ wherein x is larger than 0 and smaller than 2, y equals 2-x and each Alk, independently, represents an alkyl group, is contacted with a titanium tetraalkoxide and/or an alcohol in the presence of an inert dispersant to give an intermediate reaction product and wherein the intermediate reaction product is contacted with titanium tetrachloride in the presence of an internal donor, which is di-n-butyl phthalate.

Preferably, the Ziegler-Natta type procatalyst in the catalyst system according to the present invention is obtained by the process that is similar to the process as described in EP2027164B1. Example I including all sub-examples (IA-IE) is incorporated into the present description. More details about the different embodiments are disclosed starting in paragraphs [0016] tot [0089]. All these embodiments related to the process and products are incorporated by reference into the present description. In the following part of the description the different steps and phases of the process for preparing the procatalyst according to the present invention will be discussed.

The process for preparing a procatalyst according to the present invention comprises the following phases: phase A): preparing a solid support for the procatalyst; phase B): optionally activating said solid support obtained in phase A using one or more activating compounds to obtain an activated solid support; phase C): contacting said solid support obtained in phase A or said activated solid support in phase B with a catalytic species wherein phase C may comprise one of the following: contacting said solid support obtained in phase A or said activated solid support in phase B with a catalytic species and one or more internal donors to obtain said procatalyst; or contacting said solid support obtained in phase A or said activated solid support in phase B with a catalytic species and one or more internal donors to obtain an intermediate product; or contacting said solid support obtained in phase A or said activated solid support in phase B with a catalytic species and an activator to obtain an intermediate product; and optionally Phase D): modifying said intermediate product obtained in phase C wherein phase D may comprise one of the following: modifying said intermediate product obtained in phase C with a Group 13- or transition metal modifier in case an internal donor was used during phase C, in order to obtain a procatalyst; modifying said intermediate product obtained in phase C with a Group 13- or transition metal modifier and an internal donor in case an activator was used during phase C, in order to obtain a procatalyst.

The procatalyst thus prepared can be used in polymerization of olefins using an external donor and a co-catalyst. The various steps used to prepare the catalyst according to the present invention are described in more detail below. The catalyst according to the present invention thus prepared can be used in polymerization of olefins using an external donor and a co-catalyst.

Phase A: Preparing a Solid Support for the Catalyst.

In the process of the present invention preferably a magnesium-containing support is used. Said magnesium-containing support is known in the art as a typical component of a Ziegler-Natta procatalyst. This step of preparing a solid support for the catalyst is the same as in the prior art process. The following description explains the process of preparing magnesium-based support. Other supports may be used. Synthesis of magnesium-containing supports, such as magnesium halides, magnesium alkyls and magnesium aryls, and also magnesium alkoxy and magnesium aryloxy compounds for polyolefin production, particularly of polypropylenes production are described for instance in U.S. Pat. No. 4,978,648, WO96/32427A1, WO01/23441 A1, EP1283222A1, EP1222214B1; U.S. Pat. Nos. 5,077,357; 5,556,820; 4,414,132; 5,106,806 and 5,077,357 but the present process is not limited to the disclosure in these documents.

Preferably, the process for preparing the solid support for the procatalyst according to the present invention comprises the following steps: step o) which is optional and step i). Step o) preparation of the Grignard reagent (optional) and Step i) reacting a Grignard compound with a silane compound. Optional step o), including many embodiments, is described in detail in WO2015091984 A1 of the same applicant, page 15 line 14 to page 16, line 28, which complete section is incorporated here by reference. Step i), including many embodiments, is described in detail in WO2015091984 A1, page 16 line 30 to page 22, line 25, which complete section is incorporated here by reference.

Phase B: Activating Said Solid Support for the Catalyst.

This step of activating said solid support for the catalyst is an optional step that is not required, but is preferred, in the present invention. If this step of activation is carried out, preferably, the process for activating said solid support comprises the following step ii). This phase may comprise one or more stages. Step ii) relates to the activation of the solid magnesium compound and this step, including many embodiments, is described in detail in WO2015091984 A1 of the same applicant, page 23 line 3 to page 28, line 14, which complete section is incorporated here by reference. According to the present invention, the solid support and procatalyst preferably have an average particle size (or APS) of between 24-30 microns. The particle size is measured using a test method based on ASTM standard test method D4464-201.

Phase C: Contacting Said Solid Support with the Catalytic Species and Either One or More Internal Donors or an Activator.

Phase C: contacting the solid support with a catalytic species. This step can take different forms, such as i) contacting said solid support with the catalytic species and one or more internal donors to obtain said procatalyst; ii) contacting said solid support with a catalytic species and one or more internal donors to obtain an intermediate product; iii) contacting said solid support with a catalytic species and an activator to obtain an intermediate product. This phase C, is described in detail in WO2015091984 A1 of the same applicant, page 28 line 15 to page 31, line 13, which complete section is incorporated here by reference.

Phase C may comprise several stages (e.g. I, II and III). During each of these consecutive stages the solid support is contacted with said catalytic species. In other words, the addition or reaction of said catalytic species may be repeated one or more times. For example, during stage I of phase C said solid support (first intermediate) or the activated solid support (second intermediate) is first contacted with said catalytic species and optionally subsequently with an internal donor. When a second stage is present, during stage II the intermediate product obtained from stage I will be contacted with additional catalytic species which may the same or different than the catalytic species added during the first stage and optionally an internal donor. In case three stages are present, stage III is preferably a repetition of stage II or may comprise the contacting of the product obtained from stage II with both a catalytic species (which may be the same or different as above) and an internal donor. In other words, an internal donor may be added during each of these stages or during two or more of these stages. When an internal donor is added during more than one stage it may be the same or a different internal donor. An internal donor according to Formula A is added during at least one of the stages of Phase C.

An activator according to the present invention—if used—may be added either during stage I or stage II or stage III. An activator may also be added during more than one stage. Preferably, the process of contacting said solid support with the catalytic species and an internal donor comprises the following step iii).

Step iii) Reacting the Solid Support with a Transition Metal Halide

Step iii) reacting the solid support with a transition metal halide (e.g. titanium, chromium, hafnium, zirconium, vanadium) but preferably titanium halide. In the discussion below only the process for a titanium-base Ziegler-Natta procatalyst is disclosed, however, the application is also applicable to other types of Ziegler-Natta procatalysts. Step iii) is described in detail in WO2015091984 A1 page 29 line 28 to page 31, line 13, which complete section is incorporated here by reference. An internal electron donor is added during step iii) according to Formula A. Also mixtures of internal electron donors can be used. Examples of internal electron donors that may be used in addition to the internal electron donor according for Formula A are disclosed below. In an embodiment, only an internal electron donor according to Formula A is used. The molar ratio of the internal electron donor(s) relative to the magnesium may vary between wide limits, for instance from 0.01 to 0.75. Preferably, this molar ratio is from 0.02 to 0.4; more preferably from 0.03 to 0.2. Other optional ranges are between 0.04 to 0.08; between 0.1 and 0.4 or between 0.1 and 0.3.

Optionally an activator is present during step iii) of Phase C instead of an internal donor, this is explained in more detail below in the section of activators. The molar ratio of the activator relative to the magnesium may vary between wide limits, for instance from 0.02 to 1.0. Preferably, this molar ratio is from 0.05 to 0.8; more preferably from 0.1 to 0.6; and most preferably from 0.1 to 0.5.

Phase D: Modifying Said Intermediate Product with a Metal-Based Modifier.

This phase D is optional in the present invention. In a preferred process for modifying the supported catalyst, this phase consists of the following steps: Step iv) modifying the third intermediate product with a metal-modifier—preferably an aluminium halide, e.g. $AlCl_3$ modifier—to yield a modified intermediate product; Step v) contacting said modified intermediate product with a titanium halide and optionally on or more internal donors to obtain the present procatalyst. The order of addition, viz. the order of first step iv) and subsequently step v) is considered to be very important to the formation of the correct clusters of Group 13- or transition metal and titanium forming the modified and more active catalytic centre. Each of these steps is disclosed in more detail below. It should be noted that the steps iii), iv) and v) (viz. phases C and D) are preferably carried out in the same reactor, viz. in the same reaction mixture, directly following each other. Preferably step iv) is carried out directly after step iii) in the same reactor. Preferably, step v) is carried out directly after step iv) in the same reactor.

Step iv): Group 13- or Transition Metal Modification

This step iv) is described in detail in WO2015091984 A1 of the same applicant, page 32 line 31 to page 35, line 11, which complete section is incorporated here by reference.

Step v): Additional Treatment of Intermediate Product.

This step iv) is described in detail in WO2015091984 A1 of the same applicant, page 35 line 14 to page 37, line 14, which complete section is incorporated here by reference.

More information regarding e.g. the ratios of reaction products, weight ratio of certain components in the solid procatalyst and details regarding the procatalyst and its components are as described in WO2015091984 A1 of the same applicant (page 40 line 25 to page 41 line 23), which complete section is incorporated here by reference.

In an embodiment, an activator is present during this phase C; it may be added during any of the several stages (e.g. I, II and Ill). iii). The activator may be added during the same or a different stage as the internal electron donor. Several activators can be used, such as benzamide, alkyl-benzoates, and monoesters. Each of these will be discussed below.

A benzamide activator has a structure as disclosed in WO2015091983 A1 of the same applicant, page 13, line 13-page 14, line 37, which complete section is incorporated here by reference. Suitable non-limiting examples of "benzamides" include benzamide (BA-2H), methylbenzamide (BA-HMe) or N,N-dimethylbenzamide (BA-2Me).

Without wishing to be bound by a particular theory the present inventors believe that the fact that the most effective activation is obtained when the benzamide activator is added during stage I has the following reason. It is believed that the benzamide activator will bind the catalytic species and is later on substituted by the internal donor when the internal donor is added.

A detailed description of regarding the use of alkylbenzoates as activators is to be found in WO2015091984 A1 of the same applicant, page 42 lines 1-12, which section is incorporated here by reference. More preferably, the activator is ethylbenzoate.

A detailed description of regarding the use of mono-esters as activators is to be found in WO2015091984 A1 of the same applicant, page 42 line 12—page 43, line 24, which section is incorporated here by reference.

The catalyst system according to the present invention includes a co-catalyst. As used herein, a "co-catalyst" is a term well-known in the art in the field of Ziegler-Natta catalysts and is recognized to be a substance capable of converting the procatalyst to an active polymerization catalyst. Generally, the co-catalyst is an organometallic compound containing a metal from group 1, 2, 12 or 13 of the Periodic System of the Elements (Handbook of Chemistry and Physics, 70th Edition, CRC Press, 1989-1990). The co-catalyst may include any compounds known in the art to be used as "co-catalysts", as described in WO2015091984 A1 of the same applicant, page 59 line 1 to page 60 line 30, which is incorporated here by reference.

One of the functions of an external donor compound is to affect the stereoselectivity of the catalyst system in polymerization of olefins having three or more carbon atoms. Therefore it may be also referred to as a selectivity control agent. Examples of external donors suitable for use in the present invention are the internal donors benzoic acid esters and 1,3-diethers. In addition, the following external donors may be used:

alkylamino-alkoxysilanes, alkyl-alkoxysilane, imidosilanes, and alkylimidosilanes. The aluminum/external donor molar ratio in the polymerization catalyst system preferably is from 0.1 to 200; more preferably from 1 to 100. Mixtures of external donors may be present and may include from about 0.1 mol. % to about 99.9 mol. % of a first external donor and from about 99.9 mol. % to about 0.1 mol. % of either a second or the additional alkoxysilane external donor disclosed below. When a silane external donor is used, the Si/Ti molar ratio in the catalyst system can range from 0.1 to 80, preferably from 0.1 to 60, even more preferably from 1 to 50 and most preferably from 2 to 30.

Documents EP1538167 and EP1783145 disclose a Ziegler-Natta catalyst type comprising an organo-silicon compound as external donor that is represented by formula $Si(OR^c)_3(NR^dR^e)$, wherein $R^c$ is a hydrocarbon group having 1 to 6 carbon atoms, $R^d$ is a hydrocarbon group having 1 to 12 carbon atoms or hydrogen atom, and $R^e$ is a hydrocarbon group having 1 to 12 carbon atoms used as an external electron donor. Examples of suitable external donors according to the present invention are known from WO2015091984 A1, being compounds according to Formula III, alkyl-alkoxysilanes according to Formula IV, organosilicon compounds having formula $Si(OR^a)_{4-n}R^b_n$, imidosilanes according to Formula I, alkylimidosilanes according to Formula I' as described on page 61 line 26 to page 67 line 8 which is incorporated here by reference. Alkoxy silane halide are used for preparing imidosilane and alkylimidosilane internal donors and are, respectively, according to Formula XXIVa: $Z_nSi(OR^{11})_{4-n}$ and Formula XXIVa: $Z_nSi(OR^{11})_{4-n-m}(R^{12})_m$. In the alkoxy silane halide represented by Formula XXIVa and XXIVb, Z is halogen group, and more preferably a chlorine group; n=1, 2 or 3.

Specific examples regarding the external donor, considering Formula I' in WO2015091984 A1, are described in WO2015091984 A1 of the same applicant, page 67 lines 9-22, which is incorporated here by reference.

The additional compound(s) in the external donor according to the invention may be one or more alkoxysilanes, as described in WO2015091984 A1 of the same applicant, page 67 line 24 to page 69 line 4, which section is incorporated here by reference.

In an embodiment, the silane-compound for the additional external donor is dicyclopentyl dimethoxysilane, di-isopropyl dimethoxysilane, di-isobutyl dimethyoxysilane, methylcyclohexyl dimethoxysilane, n-propyl trimethoxysilane, n-propyltriethoxysilane, dimethylamino triethoxysilane, and one or more combinations thereof. Preferably, the external donor is an alkyl-alkoxysilane according to formula IV (preferably n-propyl trimethoxysilane or n-propyl triethoxysilane) or cyclohexylmethyldimethoxysilane or another dialkyldialkoxysilane.

The invention also relates to a process to make the catalyst system by contacting a Ziegler-Natta type procatalyst, a co-catalyst and an external electron donor.

The procatalyst, the co-catalyst and the external donor can be contacted in any way known to the skilled person in the art; and as also described herein, more specifically as in the Examples. The invention further relates to a process of preparing a polyolefin by contacting at least one olefin with a polymerization catalyst system comprising the procatalyst according to the present invention. Preferably, the polyolefin made by using the catalyst system of the present invention is a polypropylene. It is an advantage of the present invention that polyolefins are obtained in a higher yield than when non-modified prior art procatalysts are used.

For instance, the external donor in the catalyst system according to the present invention can be complexed with the co-catalyst and mixed with the procatalyst (pre-mix) prior to contact between the procatalyst and the olefin. The external donor can also be added independently to the polymerization reactor. The procatalyst, the co-catalyst, and the external donor can be mixed or otherwise combined prior to addition to the polymerization reactor. Contacting the olefin with the catalyst system according to the present invention can be done under standard polymerization conditions, known to the skilled person in the art. See for example Pasquini, N. (ed.) "Polypropylene handbook" 2$^{nd}$ edition, Carl Hanser Verlag Munich, 2005. Chapter 6.2 and references cited therein.

The polymerization process may be a gas phase, a slurry or a bulk polymerization process, operating in one or more than one reactor. One or more olefin monomers can be introduced in a polymerization reactor to react with the procatalyst and to form an olefin-based polymer (or a fluidized or agitated bed of polymer particles).

Polymerization in a slurry (liquid phase) as well as information about the polyolefins that are/may be prepared are described in WO2015091984 A1 of the same applicant, page 70 line 15 10 to page 71 line 23 which section is incorporated here by reference; information about gas-phase polymerization processes are as described in WO2015091984 A1 of the same applicant, page 71 line 25 to page 72 line 26 which is incorporated here by reference.

The olefin according to the invention may be selected from mono- and di-olefins containing from 2 to 40 carbon atoms; see also WO2015091984 A1 of the same applicant, page 72 line 28 to page 73 line 5 which section is incorporated here by reference.

Preferably, the olefin is propylene or a mixture of propylene and ethylene, to result in a propylene-based polymer, such as propylene homopolymer or propylene-olefin copolymer. The olefin may an alpha-olefin having up to 10 carbon atoms, such as ethylene, butene, hexene, heptene, octene.

The present invention also relates to a polyolefin, preferably a polypropylene obtained or obtainable by a process, comprising contacting an olefin, preferably propylene or a mixture of propylene and ethylene with the procatalyst according to the present invention. More information about the polymers formed is disclosed WO2015091984 A1 of the same applicant, page 73 lines 6-23 and 25-34 and page 74 line 26 page 75, line 24 which section is incorporated by reference entirely. The present invention also relates to a polyolefin, preferably a propylene-based polymer obtained or obtainable by a process as described herein above, comprising contacting propylene or a mixture of propylene and ethylene with a catalyst system according to the present invention. In one embodiment the present invention relates to the production of a homopolymer of polypropylene. Several polymer properties are discussed here.

Xylene soluble fraction (XS) is preferably lower than 12 wt %, such as from about 0.5 wt % to about 10 wt %, or from about 1 wt % to about 8 wt %, or from 2 to 6 wt %.

The production rate is preferably from about 1 kg/g/hr to about 100 kg/g/hr, or from about 20 kg/g/hr to about 90 kg/g/hr. MFR is preferably from about 0.01 g/10 min to about 2000 g/10 min, or from about 0.01 g/10 min to about 1000 g/10 min; or from about 0.1 g/10 min to about 500 g/10 min, or from about 0.5 g/10 min to about 150 g/10 min, or from about 1 g/10 min to about 100 g/10 min.

Polyolefins having medium molecular weight distribution are herein polyolefins that may have a $M_w/M_n$ between 5.0 and 7.0 or between 5.0 and 6.5, for example between 5.5 and 6.0. These polyolefins are preferred.

A high isotacticity of the polyolefins obtained with the procatalyst according to the present invention indicates low amount of amorphous atactic polymer (APP) in the products obtained, such as for example lower than 3 wt. %, lower than 2 wt. % or even lower than 1 wt. % of the total amount of polymer.

The methods used in the present invention to determine the molecular weight distribution, the amount of atactic polymer, the xylene solubles content and melt flow range are described above.

The invention also relates to the use of the polyolefins, preferably the propylene-based polymers (also called polypropylenes) according to the invention in injection moulding, blow moulding, extrusion moulding, compression moulding, casting, thin-walled injection moulding, etc. for example in food contact applications. Furthermore, the invention relates to a shaped article comprising the polyolefin, preferably the propylene-based polymer according to the present invention.

The polyolefin, preferably the propylene-based polymer according to the present invention may be transformed into shaped (semi)-finished articles using a variety of processing techniques. Examples of suitable processing techniques include injection moulding, injection compression moulding, thin wall injection moulding, extrusion, and extrusion compression moulding. Injection moulding is widely used to produce articles such as for example caps and closures, batteries, pails, containers, automotive exterior parts like bumpers, automotive interior parts like instrument panels, or automotive parts under the bonnet. Extrusion is for example widely used to produce articles, such as rods, sheets, films and pipes. Thin wall injection moulding may for example be used to make thin wall packaging applications both for food and non-food segments. This includes pails and containers and yellow fats/margarine tubs and dairy cups.

It is noted that the invention relates to all possible combinations of features recited in the claims. Features described in the description may further be combined.

Although the invention has been described in detail for purposes of illustration, it is understood that such detail is solely for that purpose and variations can be made therein by those skilled in the art without departing from the spirit and scope of the invention as defined in the claims. It is further noted that the invention relates to all possible combinations of features described herein, preferred in particular are those combinations of features that are present in the claims. It is further noted that the term 'comprising' does not exclude the presence of other elements. However, it is also to be understood that a description on a product comprising certain components also discloses a product consisting of these components. Similarly, it is also to be understood that a description on a process comprising certain steps also discloses a process consisting of these steps.

The invention will be further elucidated with the following examples without being limited hereto.

EXAMPLES

Example A

Preparation of ethyl (4-(N-methylbenzamido)pentan-2-yl) carbonate

Step 1:

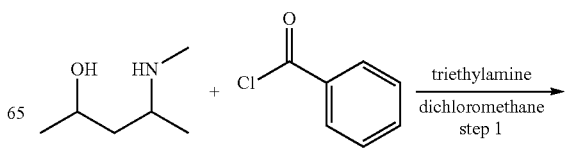

-continued

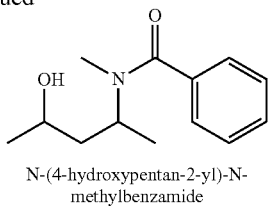

N-(4-hydroxypentan-2-yl)-N-methylbenzamide 4-(methylamino)pentan-2-ol (15 gm, 0.127 mole) was added under nitrogen to a mixture of triethylamine (15 ml, 0.127 mole) and methylenedichloride (100 ml). The mass was cooled to 10° C. and benzoyl chloride (16 gm, 0.102 mol) was added drop wise.

The mixture was stirred for 4 hours at 25° C. On completion of reaction was quenched in aqueous HCl. The organic layer is washed with water until neutral pH, dried on anhydrous sodium sulfate and solvent is distilled to afford 22 gm (91.66%) N-(4-hydroxypentan-2-yl)-N-methylbenzamide which is used in further step without purification Step 2:

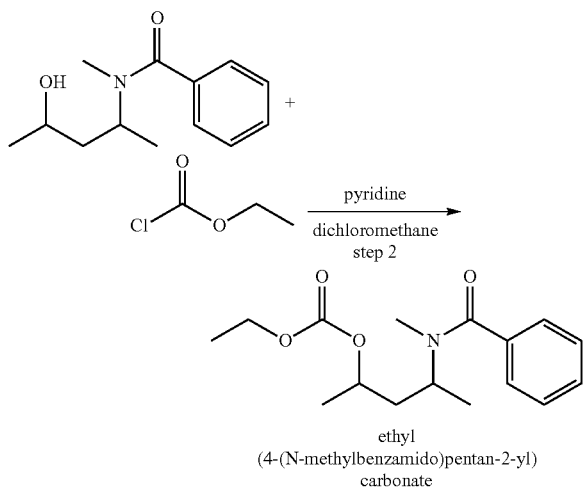

ethyl (4-(N-methylbenzamido)pentan-2-yl) carbonate

N-(4-hydroxypentan-2-yl)-N-methylbenzamide (22.1 gm, 0.1 mole) and ethyl chloroformate (11.8 gm, 0.1 mole) was charged in a round bottom flask, with 150 ml of $CH_2Cl_2$ under nitrogen. The solution is cooled to −10° C., then pyridine (20 gm) is added drop wise slowly. The mixture brought to room temperature and stirred for 4 hours and quenched in dilute HCl. The organic layer washed with water until neutral pH, dried over anhydrous sodium sulphate and solvent is distilled off to afford 29.3 gm (99%) of ethyl (4-(N-methylbenzamido)pentan-2-yl)carbonate.

Example 1

Step A) Butyl Grignard Formation

A 1.7 L stirred flask, fitted with a reflux condenser and a funnel, was filled with magnesium powder (40.0 g, 1.65 mol). The flask was brought under nitrogen. The magnesium was dried at 80° C. for 2 hours under nitrogen purge, after which dibutyl ether (200 ml), iodine (0.05 g) and n-chlorobutane (10 ml) were successively added and stirred at 120 rpm. The temperature was maintained at 80° C. and a mixture of n-chlorobutane (146 ml) and dibutyl ether (1180 ml) was slowly added over 3 hours. The reaction mixture was stirred for another 3 hours at 80° C. Then the stirring and heating were stopped and the small amount of solid material was allowed to settle for 24 hours. By decanting the colourless solution above the precipitate, a solution of butyl magnesium chloride with a concentration of 0.90 mol Mg/L was obtained.

Step B) Preparation of the First Intermediate Reaction Product

The solution of reaction product of step A (500 ml, 0.45 mol Mg) and 260 ml of a solution of tetraethoxysilane (TES) in dibutyl ether (DBE), (47 ml of TES and 213 ml of DBE), were cooled to 5° C., and then were fed simultaneously to a mixing device (minimixer) of 0.45 ml volume equipped with a stirrer and jacket. The minimixer was cooled to 5° C. by means of cold water circulating in the minimixer's jacket. The stirring speed in the minimixer was 1000 rpm. From the mixing device, the mixed components were directly dosed into a 1.3 liter reactor fitted with blade stirrer and containing 350 ml of dibutyl ether. The dosing temperature of the reactor was 35° C. and the dosing time was 360 min. The stirring speed in the reactor was 250 rpm at the beginning of dosing and was gradually increased up to 450 rpm at the end of dosing stage. On completion of the dosing, the reaction mixture was heated up to 60° C. in 30 minutes and held at this temperature for 1 hour. Then the stirring was stopped and the solid substance was allowed to settle. The supernatant was removed by decanting. The solid substance was washed three times using with 700 ml of heptane at a reactor temperature of 50° C. for three times. A pale yellow solid substance, reaction product B (the solid first intermediate reaction product; the support), was obtained upon drying with a nitrogen purge. The average particle size of support was 20 µm.

Step C) Preparation of the Activated Support

Step C1) First Activation Step

In inert nitrogen atmosphere at 20° C. in a 1000 ml glass flask equipped with a mechanical agitator was filled with 50 g of reaction product B, dispersed in 500 ml of heptane and stirred at 250 rpm. Subsequently, a solution of 2.7 ml ethanol (EtOH/Mg=0.1) in 20 ml heptane was dosed under stirring during 1 hour. After keeping the reaction mixture at 20° C. for 30 minutes, a solution of 9.5 ml titanium tetraethoxide (TET/Mg=0.1) in 20 ml of heptane was added for 1 hour. The slurry was slowly allowed to warm up to 30° C. over 30 minutes and held at that temperature for another 2 hours. Finally, the supernatant liquid was decanted from the solid reaction (partly activated support) which was washed once with 500 ml of heptane at 30° C. and dried using a nitrogen purge.

Step C2) Second Activation Step

In inert nitrogen atmosphere at 25° C. in a 1000 ml glass flask equipped with a mechanical agitator was filled with 50 g of partly activated support obtained in step C1 dispersed in 500 ml of heptane and stirred at 250 rpm. Subsequently, a solution of 6.3 ml ethanol (EtOH/Mg=0.3), 20.8 ml of toluene and 37.5 ml of heptane was dosed at 25° C. under stirring during 1 hour. The slurry was slowly allowed to warm up to 30° C. over 30 minutes and held at that temperature for another 3 hours. Finally, the supernatant liquid was decanted from the solid reaction product (second intermediate reaction product; activated support) which was washed once with 500 ml of heptane at 25° C. and dried using a nitrogen purge.

Step D) Preparation of the Procatalyst A

Stage I of Procatalyst Preparation

A 300 ml reactor-filter flask was brought under nitrogen and 125 mL of titanium tetrachloride was added, then 5.5 g of activated support obtained in step C2 in 15 ml of heptane was added to the reactor. The contents of the reactor were stirred for 60 minutes at room 25° C. Then, 0.83 ml of ethylbenzoate, EB (EB/Mg=0.30 molar ratio) in 4 ml of chlorobenzene was added to the reactor in 30 minutes. Temperature of reaction mixture was increased to 105° C. and then the reaction mixture was stirred at 105° C. for 90 minutes. The contents of the flask were filtered, after which the solid product was washed with chlorobenzene (125 ml) at 100 to 105° C. for 20 minutes. Then, the contents of the flask were filtered.

Stage II of Procatalyst Preparation

A mixture of titanium tetrachloride (62.5 ml) and chlorobenzene (62.5 ml) was added to the reactor. Then, 0.438 g of the internal donor as prepared in Example A (ID/Mg=0.03) in 4 ml of chlorobenzene was added to the reactor in 10 minutes. The reaction mixture was stirred at 105° C. for 60 minutes. Then, the contents of the flask were filtered.

Stage III of Procatalyst Preparation

A mixture of titanium tetrachloride (62.5 ml) and chlorobenzene (62.5 ml) was added to the reactor. Then, 0.438 g of the internal donor as prepared in Example A (ID/Mg=0.03) in 4 ml of chlorobenzene was added to the reactor in 10 minutes. The reaction mixture was stirred at 105° C. for 60 minutes. Then, the contents of the flask were filtered.

Stage IV of Procatalyst Preparation

A mixture of titanium tetrachloride (62.5 ml) and chlorobenzene (62.5 ml) was added to the reactor. Then, 0.438 g of the internal donor as prepared in Example A (ID/Mg=0.03) in 4 ml of chlorobenzene was added to the reactor in 10 minutes. The reaction mixture was stirred at 105° C. for 30 minutes. Then, the contents of the flask were filtered.

Work Up of Procatalyst Preparation

The solid product obtained was washed five times with 125 ml of heptane starting at 60° C. with 5 minutes stirring per wash prior to filtration. The temperature was gradually reduced from 60 to 25° C. during the washings. Finally, the solid product obtained was dried using a nitrogen purge at a temperature of 25° C. for 2 hours. The composition of the procatalyst A produced is given in Table 1.

Comparative Example 1 Preparation of the Procatalyst CE-A

Comparative Example 1 was carried out in the same way as Example 1 except that in stages II, III and IV of step D 0.36 g of 4-[(ethoxycarbonyl)(methyl)amino]pentan-2-yl-ethyl carbamate (AB-OEt/Mg=0.03) was used instead of 0.438 g of ethyl (4-(N-methylbenzamido)pentan-2-yl) carbonate. The synthesis of AB-Oet is discussed in WO2015/185489, Example A. The composition of the procatalyst CE-A produced is given in Table 1.

Polymerization of Propylene

Liquid pool propylene polymerization was carried out in a one gallon bench scale reactor. The method of polymerization involved baking the polymerization reactor at 110° C. for 60 min, applying three high pressure (15 bar) nitrogen purges at 110° C., then lowering the reactor temperature to 30° C. whilst purging the reactor with nitrogen. Then the reactor was purged three times, with 50 g of propylene for each purge. Then, 1.375 kg of liquid propylene was introduced to the reactor followed by the addition of 200 psig hydrogen to the reactor from an 75 mL stainless steel cylinder.

The reactor temperature was then raised to 62° C., and stirring speed set to 500 rpm. Then, 0.25 mmol of the neat external electron donor, cyclohexylmethyldimethoxysilane, was injected to the reactor. Then, 2.0 mmol of co-catalyst, triethylaluminium was injected in the reactor. Then procatalyst, corresponding to 0.01 mmol Ti, was injected to the reactor. The reactor temperature was raised to 67° C. and the stirring speed increased to 1500 rpm and polymerization was carried out for one hour.

After this period, the propylene in the reactor was vented and the product polypropylene was obtained. The yield was determined after allowing the product to dry. Polymerization and product analysis results are given in Table 2.

TABLE 1

| Procat. | Examples | d50 [µm] | Mg [%] | Ti [%] | ID [%] | EtOH [%] | EB [%] |
|---|---|---|---|---|---|---|---|
| A | Ex 1 | 21.90 | 19.88 | 2.25 | 6.20 | 1.48 | 2.02 |
| CE-A | Comp. Ex 1 | 22.52 | 18.25 | 2.58 | 3.38 | 1.01 | 2.06 |

TABLE 2

| Procat. | Examples | Productivity [kg/g cat] | Bulk Density [kg/m3] | Mw [g/mol] | Mn [g/mol] | MWD | XS [%] |
|---|---|---|---|---|---|---|---|
| A | Ex 2 | 20.0 | 348 | 404900 | 65500 | 6.2 | 2.46 |
| CE-A | Comp. Ex 2 | 31.2 | 400 | 382364 | 68168 | 5.6 | 2.02 |

Hence one or more of the objections of the present invention are obtained by using an internal donor according to Formula A.

The invention claimed is:

1. A procatalyst for the polymerization of olefins, which procatalyst comprises a compound represented by Formula A as an internal electron donor:

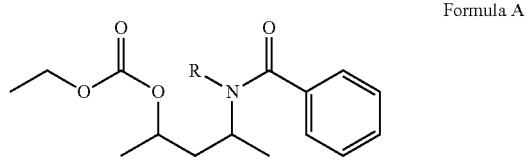

Formula A wherein R is hydrogen or a methyl group.

2. The procatalyst according to claim 1, wherein R is hydrogen, said procatalyst being ethyl (4-benzamidopentan-2-yl) carbonate, being of the formula:

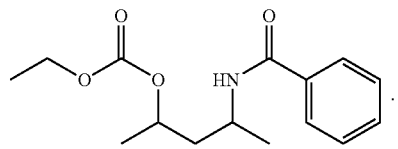 [SMILES: CCOC(=O)OC(C)CC(C)NC(=O)c1ccccc1]

3. The procatalyst according to claim 1, wherein R is a methyl group, said procatalyst being ethyl (4-(N-methylbenzamido)pentan-2-yl) carbonate, being of the formula:

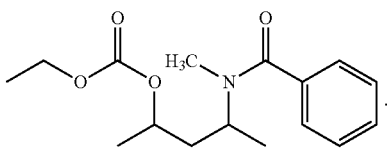 [SMILES: CCOC(=O)OC(C)CC(C)N(C)C(=O)c1ccccc1]

4. The procatalyst according to claim 1, wherein said procatalyst comprises titanium supported on a solid magnesium-containing support.

5. A process for preparing the procatalyst according to claim 1, said process comprising contacting a magnesium-containing support with a halogen-containing titanium compound and an internal electron donor, wherein the internal electron donor is a compound represented by formula A,

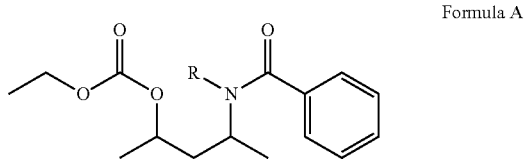

Formula A wherein R is hydrogen or a methyl group.

6. The process according to claim 5, which process comprises the steps of:
  i) contacting a compound $R^4_z MgX^4_{2-z}$ with an alkoxy- or aryloxy-containing silane compound to give a first intermediate reaction product, being a solid $Mg(OR^1)_x X^1_{2-x}$, wherein: $R^4$ and $R^1$ are each a linear, branched or cyclic hydrocarbyl group independently selected from alkyl, alkenyl, aryl, aralkyl, alkoxycarbonyl or alkylaryl groups, and one or more combinations thereof; wherein said hydrocarbyl group may be substituted or unsubstituted, and may contain one or more heteroatoms; $X^4$ and $X^1$ are each independently selected from the group consisting of fluoride (F—), chloride (Cl—), bromide (Br—) and iodide (I—); z is in a range of larger than 0 and smaller than 2, being 0<z<2; x is in a range of larger than 0 and smaller than 2, being 0<x<2;
  ii) optionally contacting the first intermediate reaction product obtained in step i) with at least one activating compound selected from the group consisting of activating electron donors and metal alkoxide compounds of formula $M^1(OR^2)_{v-w}(OR^3)_w$ or $M^2(OR^2)_{v-w}(R^3)_w$, to obtain a second intermediate product; wherein: $M^1$ is a metal selected from the group consisting of Ti, Zr, Hf, Al, and Si; $M^2$ is a metal being Si; v is the valency of $M^1$ or $M^2$; w is smaller than v; $R^2$ and $R^3$ are each a linear, branched or cyclic hydrocarbyl group independently selected from alkyl, alkenyl, aryl, aralkyl, alkoxycarbonyl or alkylaryl groups, and one or more combinations thereof; wherein said hydrocarbyl group may be substituted or unsubstituted, and may contain one or more heteroatoms; and
  iii) contacting the first or second intermediate reaction product, obtained respectively in step i) or ii), with a halogen-containing Ti-compound and said internal electron donor being a compound represented by Formula A.

7. The process according to claim 6, wherein in step ii) the first intermediate reaction product obtained in step i) is contacted with two activating compounds, being an alcohol as the activating electron donor, and a titanium tetraalkoxide as the metal alkoxide compound.

8. The process according to claim 6, wherein in step (iii), the first or second intermediate reaction product, obtained respectively in step i) or ii), is contacted with the halogen-containing Ti-compound and an activator selected from the group consisting of benzamides, alkylbenzoates, and monoesters.

9. A polymerization catalyst system comprising the procatalyst according to claim 1, a co-catalyst and optionally an external electron donor.

10. A process of making a polyolefin, comprising contacting an olefin with the catalyst system according to claim 9.

11. A polyolefin obtained by the process according to claim 10, wherein the polyolefin comprises the polymerization catalyst system.

12. A shaped article, comprising the polyolefin according to claim 11.

13. A compound represented by formula A

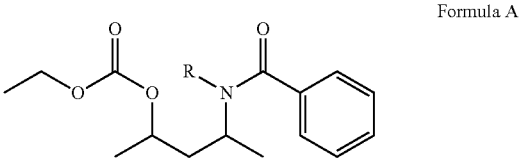

Formula A wherein R is hydrogen or a methyl group.

14. The compound of claim 13, being ethyl (4-benzamidopentan-2-yl) carbonate of the formula:

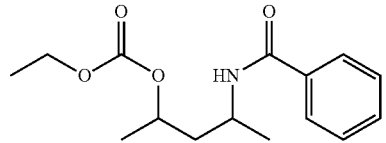 [SMILES: CCOC(=O)OC(C)CC(C)NC(=O)c1ccccc1]

or ethyl (4-(N-methylbenzamido)pentan-2-yl) carbonate of the formula:

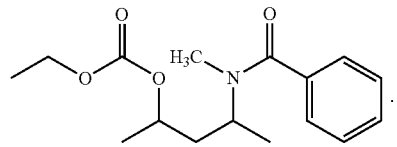 [SMILES: CCOC(=O)OC(C)CC(C)N(C)C(=O)c1ccccc1]

15. The process according to claim 4, wherein said procatalyst comprises in wt. % based on the total weight of the procatalyst: magnesium: from 13 to 24; and titanium: from 1 to 5.

16. The process according to claim 8, wherein the activator is a monoester is selected from the group consisting of butyl formate, ethyl acetate, amyl acetate, butyl acetate, ethyl acrylate, methyl methacrylate, isobutyl methacrylate, ethyl p-methoxy benzoate, methyl p-ethoxybenzoate, ethyl p-ethoxybenzoate, ethyl benzoate, methyl benzoate, propyl benzoate, ethyl p-chlorobenzoate, ethyl p-bromobenzoate, methyl-p-toluate and ethyl-naphthate.

17. The process according to claim 10, wherein the olefin is propylene.

* * * * *